US00PP08698P

United States Patent [19]

de Jong

[11] Patent Number: Plant 8,698

[45] Date of Patent: Apr. 19, 1994

[54] ALSTROEMERIA NAMED SANCERRE

[75] Inventor: Cornelis T. J. de Jong, Roelofarendsveen, Netherlands

[73] Assignee: Agroplant-Select B.V., De Kwakel, Netherlands

[21] Appl. No.: 36,655

[22] Filed: Mar. 24, 1993

[51] Int. Cl.[5] ..... A01H 5/00

[52] U.S. Cl. ..... Plt./87.1

[58] Field of Search ..... Plt. 87.1

*Primary Examiner*—James R. Feyrer

[57] ABSTRACT

A new and distinct cultivar of Alstroemeria plant named Capri, having an unusually attractive predominantly white flower with outer petals having green tips and lavender-pink brush stroke patterns in the central basal portions and inner petals which are white with faintly lavender-pink shadings and patterns of numerous purple stripes on the top two inner petals, and few purple stripes confined to the apical portion of the bottom inner petal.

1 Drawing Sheet

BACKGROUND OF THE INVENTION

The present invention comprises a new and distinct cultivar of Alstroemeria plant referred to by the cultivar name Capri. Capri was originated from a hybridization program in Roelofarendsveen, The Netherlands in 1985. The female parent was an unnamed proprietary hybrid which was developed and is maintained by me for the sole use in planned breeding programs. The male parent was a cultivar named Flamingo. It is unknown to me if Flamingo has been patented in the U.S.A. Capri was discovered and selected as one flowering plant within the progeny of the stated parentage by me on Jul. 12, 1985 in a controlled environment in Roelofarendsveen, The Netherlands. The first asexual reproduction of Capri was accomplished when vegative cuttings were taken from initial selection on Nov. 6, 1985 in a controlled environment in Roelofarendsveen in The Netherlands. Horticultural examination of selected units initiated in November 1985 has demonstrated that the combination of characteristics as herein disclosed for Capri are firmly fixed and retained through generations of asexual reproduction. The following observations, measurements and comparisons describe plants grown in Roelofarendsveen, The Netherlands under greenhouse conditions which approximate those generally used in commercial practice. The following traits have been repeatedly observed and are determined to be basic characteristics of Capri, which in combination distinguish this Alstroemeria from its parents and all other varieties of which I am aware:

1. The outer petals have an attractive, nearly white appearance which is interrupted by the green color of the tips which radiates from the tips along the central veins of each outer petal, fading to white. Along the same veins, between the attachment points and the green of the tips of these petals are brush strokes of shades of lavender-pink which compliment the green portions in shape. The remaining marginal areas of the outer petals contrastingly appear to be stark white.
2. The inner petals are characterized by an unusual combination of colors and pattern of stripes. The three inner petals have a predominant white ground color which is slightly blushed with a hint of lavender-pink. The two top inner petals have numerous stripes of deep purple in a uniform pattern with stripes increasing in length and width from the attachment point to the apex of these petals. The lower, inner petal is substantially white and has a few stripes of deep purple confined to the apical portions of this petal.
3. The soft, complimentary coloration of the petals of the flowers of this plant give striking and attractive distinction to this variety which has not been seen in previous plants of this market class.

BRIEF DESCRIPTION OF THE FIGURE OF THE DRAWING

The accompanying photographic drawing of a close-up of the flower in blooom and buds shows typical inflorescence and foliage characteristics of Capri nearly as true as possible with illustrations of this type. In the following description, color references are made to The Royal Horticultural Society Color Chart (RHS). The color values were determined in the afternoon in May 1988 at Roelofarendsveen, The Netherlands.

BOTANICAL DESCRIPTION OF THE PLANT

Botanical: Alstroemeria cv Capri.
Commercial: Alstroemeria.

PLANT

A. General appearance:

*Form.*—Typical of genus, of less than average height for the market class.

*Height.*—Average 112 cm, measured from the surface of the soil to the highest flowers. Height varies with season and light intensity. If grown as a bedding plant outside, the height is about 40 cm during the summer, and about 50 cm during the winter.

*Growth.*—Normal, upright bush forming, continuously spreading by rhizomes.

This plant is used for cut flower production.

B. Foliage:

*Quantity.*—Medium-abundant.

*Stems.*—When mature: about 40–60 per plant, per year.

*Number of leaves.*—Varying from season to season throughout the year.

*Internode.*—Length: about 10 cm; depending on light intensity and season.

*Size of leaf.*—Length: Long, about 10 cm. Width: Broad, about 4 cm.

*Shape of leaf.*—Elliptical.

*Color of leaf.*—Typical for genus. Upper side: dark green. Under side: green.

*Texture.*—Smooth.

C. Rhizomes:

*Color.*—White.

*Size.*—Average.

INFLORESCENCE

A. Bud:

*Form.*—Normal.

*Size.*—Diameter: average 2.5 cm, just prior before opening. Length: average 5 cm.

*Receptacle.*—Broadly elliptical.

B. Flower:

*Size.*—Width: about 8 cm. Depth: about 4 cm.

*Borne.*—Umbel of about 5 branches of substantially uniform length; each bearing about 5 or more buds on short peduncles.

*Blooming habit.*—When grown under controlled conditions: continuous whole year round. (Photoperiod control is required for continuous flower induction and production).

*Shape.*—Cupped to nearly flat.

*Color.*—Outer petals: Shape: lobed Color: Nearly white, which is interrupted by the green color of the tips which radiates from the tips along the central veins of each outer petal, fading to white. Along the same veins, between the attachment points and the green of the tips of these petals have brush strokes of shades of lavender-pink RHS 65-A/73-C which compliment the green portions in shape. The remaining marginal areas of the outer petals contrastingly appear to be stark white. Reverse side: same as upper surface. Size: Length: about 4 cm. Width: about 2 cm. Margins: finely dentate. Inner petals: Shape: lanceolate. Color: Upper petals: near to RHS 155-A with hue near to RHS 154-D and moderate small dark purple stripes in a uniform pattern with stripes increasing in length and width from the attachment point to the apex of these petals. Bottom petal: Substantially white, near to RHS 155-A with few stripes of deep purple confined to the apical portions of this petal. Reverse side: substantially white with few purple streaks. Size: upper petals: Length: about 3 cm; Width: about 1-1.5 cm. bottom petal: Length: about 3 cm; Width: about 1-1.5 cm. Margins: irregular undulations.

*Peduncle.*—Color: Medium green. Length: Average 12.5 cm.

*Fragrance.*—None.

*Lasting quality.*—Approximately 14 days. Petals hang on and dry.

*Flower production.*—High.

C. Reproductive organs:

*Stamens.*—Number: 6.

*Anthers.*—Color: yellow-green.

*Filaments.*—Color: purple-pink.

*Pistils.*—Color: Strong anthocyanin. Number: 1.

*Stigma.*—Color: Anthocyanin.

*Size.*—Typical for genus.

*Fertility.*—Very high.

This plant most nearly resembles the Alstroemeria plant Pisa, but is distinguished particularly by the shorter stems, moderate and small streaking on the inner petals, and the strong Anthocyanin coloring of the pistil.

I claim:

1. A new and distinct cultivar of Alstroemeria plant named Capri, as illustrated and described herein, having an unusually attractive predominantly white flower with outer petals having green tips and lavender-pink brush stroke patterns in the central basal portions and inner petals which are white with faintly lavender-pink shadings and patterns of numerous purple stripes on the top two inner petals, and few purple stripes confined to the apical portion of the bottom inner petal.

* * * * *

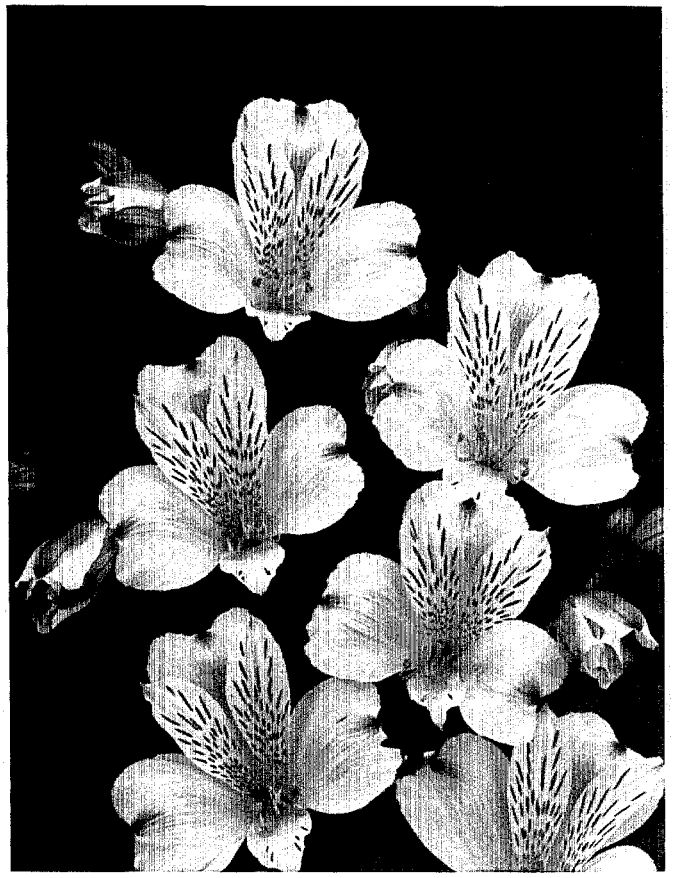

UNITED STATES PATENT AND TRADEMARK OFFICE

CERTIFICATE OF CORRECTION

PATENT NO. : Plant 8,698
DATED : April 19, 1994
INVENTOR(S) : Cornelis-Theodorus-Jacobus De Jong It is certified that error appears in the above-indentified patent and that said Letters Patent is hereby corrected as shown below:

On the title page, item [54],
In the title, change "Sancerre" to --'Capri'--.

Signed and Sealed this

Nineteenth Day of August, 1997

*Attest:*

Bruce Lehman

BRUCE LEHMAN

*Attesting Officer*

*Commissioner of Patents and Trademarks*